United States Patent [19]

Eveleigh et al.

[11] Patent Number: 4,628,029

[45] Date of Patent: Dec. 9, 1986

[54] **METHOD FOR THE CONVERSION OF A CELLULOSIC SUBSTRATE TO GLUCOSE USING *MICROBISPORA BISPORA*, STRAIN RUTGERS P&W**

[75] Inventors: Douglas E. Eveleigh, Rocky Hill, N.J.; Clarence R. Waldron, Napoleon, Ohio; Timothy Bartley, Piscataway, N.J.

[73] Assignee: Parsons & Whittemore, Inc., New York, N.Y.

[21] Appl. No.: 526,407

[22] Filed: Aug. 25, 1983

[51] Int. Cl.$^4$ .................... C12P 19/14; C12P 19/02; C12P 1/04; C12N 9/42; C12N 1/20; D21C 1/00; D21C 3/00

[52] U.S. Cl. .................... 435/99; 435/253; 435/105; 435/165; 435/170; 435/209; 435/277; 435/278

[58] Field of Search .................. 435/99, 105, 165, 170, 435/209, 254, 259, 277, 822, 253

[56] References Cited

U.S. PATENT DOCUMENTS 3,764,475 10/1973 Mandels .......................... 195/33 R
4,472,504 9/1981 Gallo .................................. 435/209

*Primary Examiner*—Thomas G. Wiseman
*Assistant Examiner*—Robin Lyn Teskin
*Attorney, Agent, or Firm*—Kenyon & Kenyon

[57] ABSTRACT

A method is described for the enzymatic saccharification of a cellulosic substrate to glucose which utilizes fermentation of the substrate with the cellulase enzyme complex-producing, thermophilic microorganism *Microbispora bispora* Rutgers P&W and its mutants. The resistance of *M. bispora* Rutgers P&W cellulase to end-product inhibition enables conversion efficiency superior to that of known cellulase producing microorganisms. Continued enzyme activity at elevated temperatures allows broader applicability of enzyme-catalyzed saccharification than heretofore attained. The microorganism in its purified form incubated on cellulase, and its cellulolytic mutants, are also disclosed.

45 Claims, 15 Drawing Figures

FIG. 1A
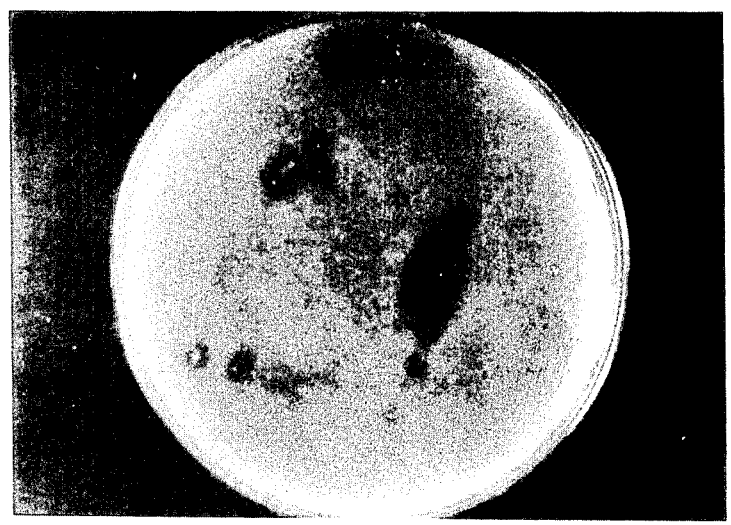
FIG. 1B

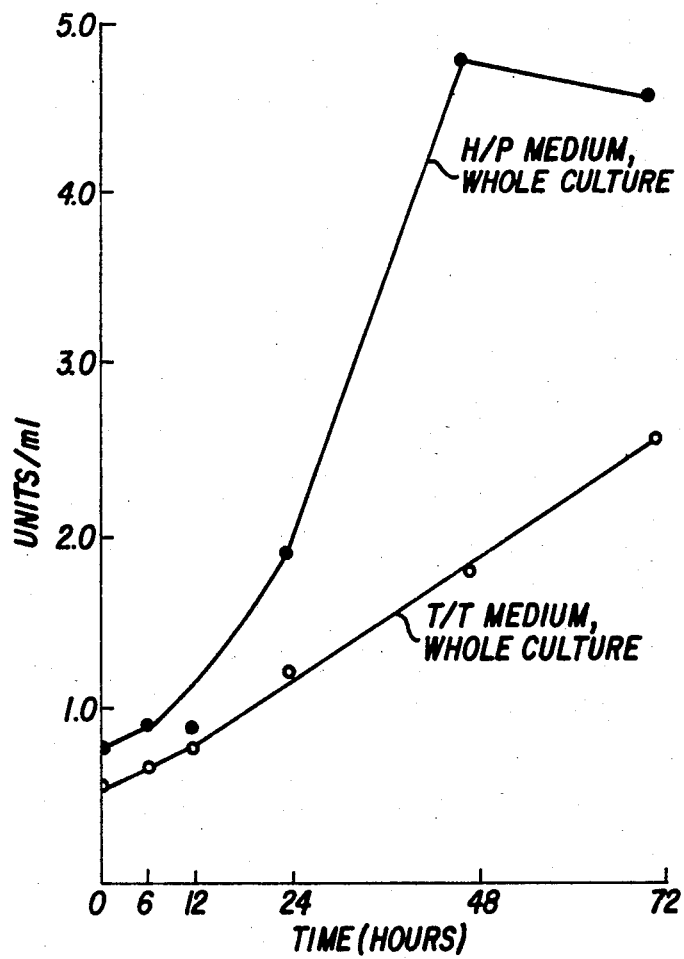
FIG. 2 ENDO-GLUCANASE (CMCase) PRODUCTION BY MICROBISPORA b.R. P&W AT 55°C

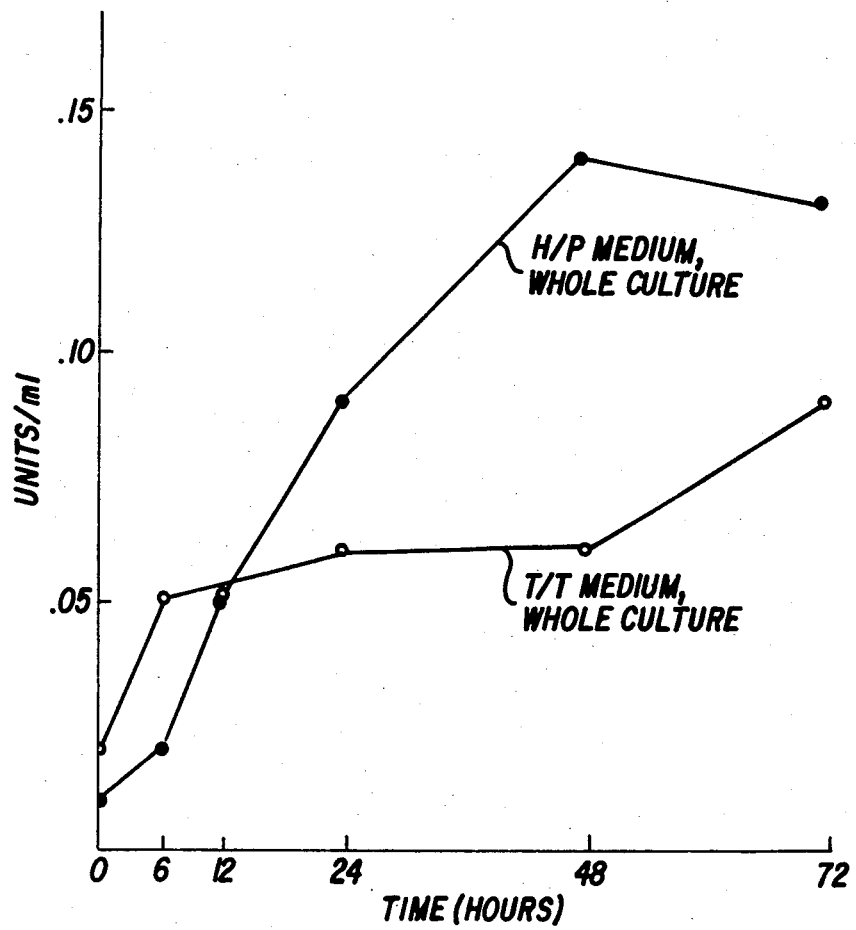
FIG. 3 B-GLUCOSIDASE (p-NPGase) PRODUCTION BY MICROBISPORA b.R. P&W AT 55°C

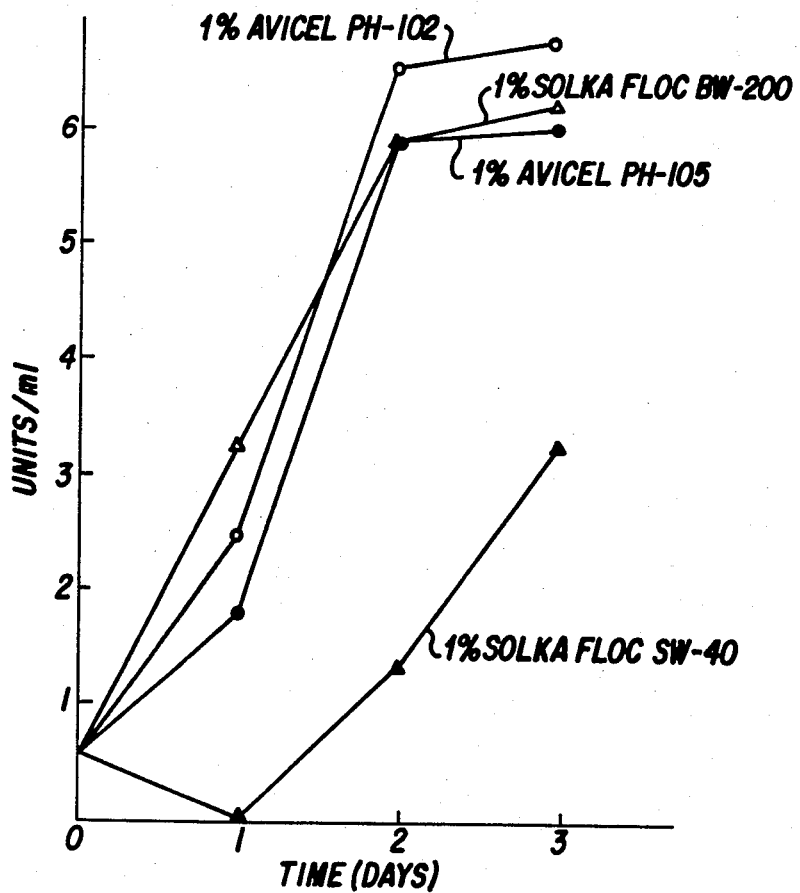
FIG. 4 EFFECT OF CARBOHYDRATE SOURCE ON ENDO-GLUCANASE (CMCase) PRODUCTION BY MICROBISPORA b.R. P&W, H/P MEDIUM, WHOLE CULTURE AT 55°C

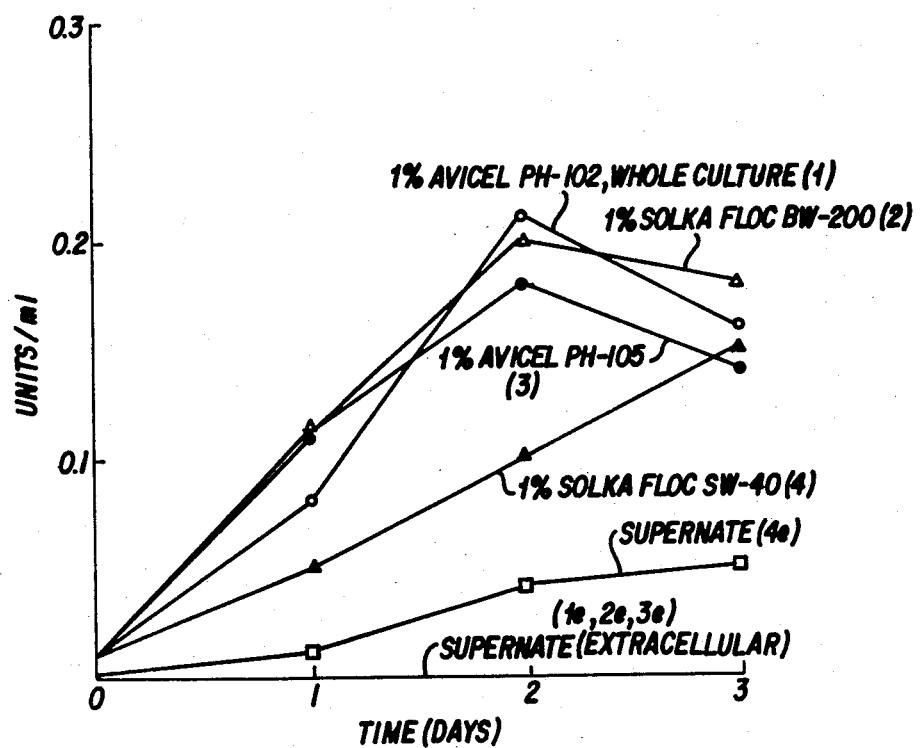
FIG. 5 EFFECT OF CARBOHYDRATE SOURCE ON B-GLUCOSIDASE (p-NPGase) PRODUCTION BY MICROBISPORA b. R. P&W H/P MEDIUM AT 55°C

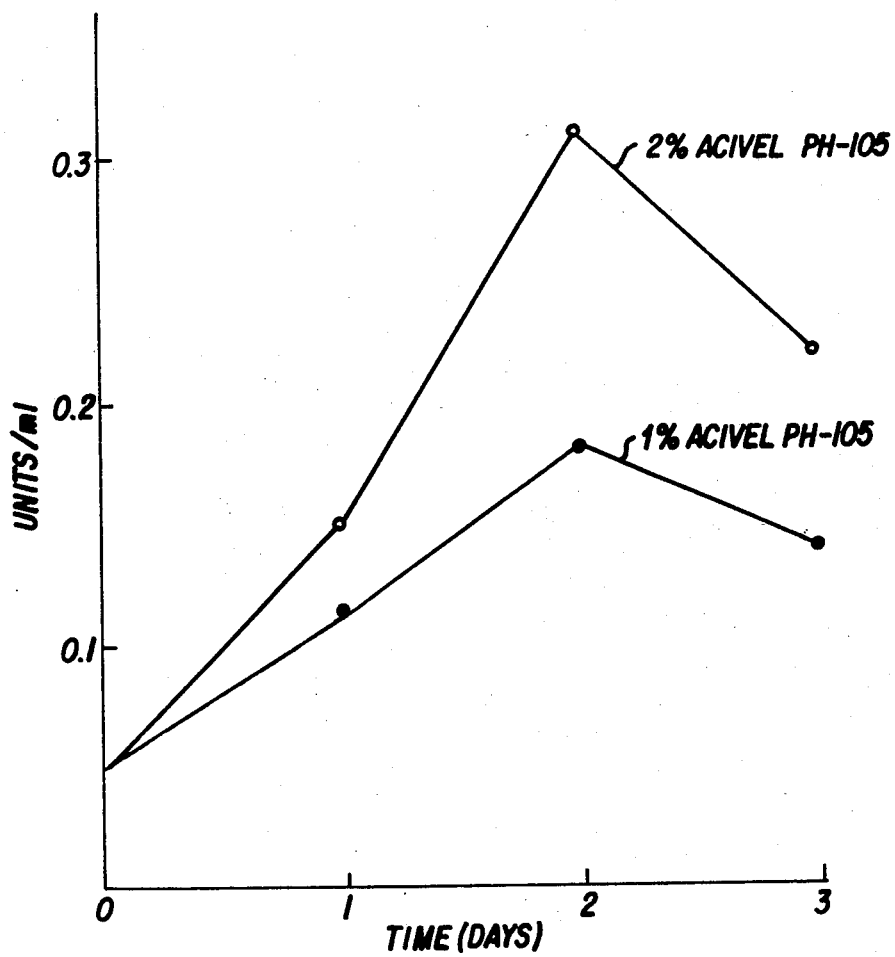
FIG. 6 EFFECT OF SUBSTRATE CONCENTRATION ON B-GLUCOSIDASE (p-NPGase) PRODUCTION BY MICROBISPORA b. R. P&W H/P MEDIUM, WHOLE CULTURE, AT 55°C

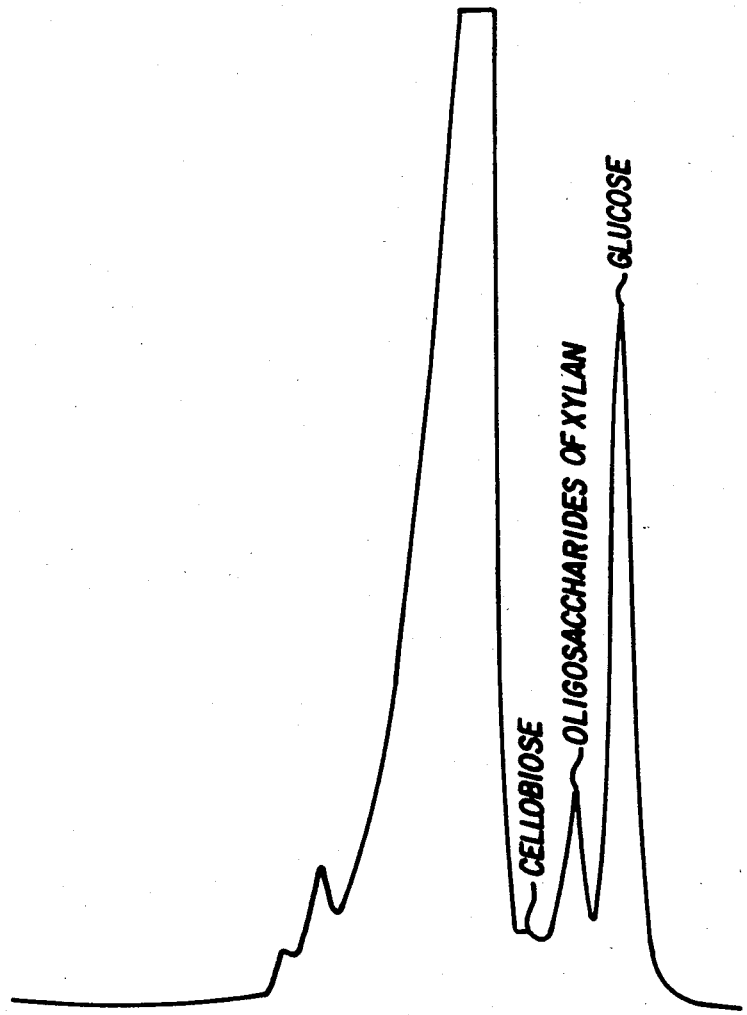
FIG. 7  SACCHARIFICATION BY ENZYME OF MICROBISPORA b. R. paw H/P MEDIUM, WHOLE CULTURE, 72 HOURS AT 55°C

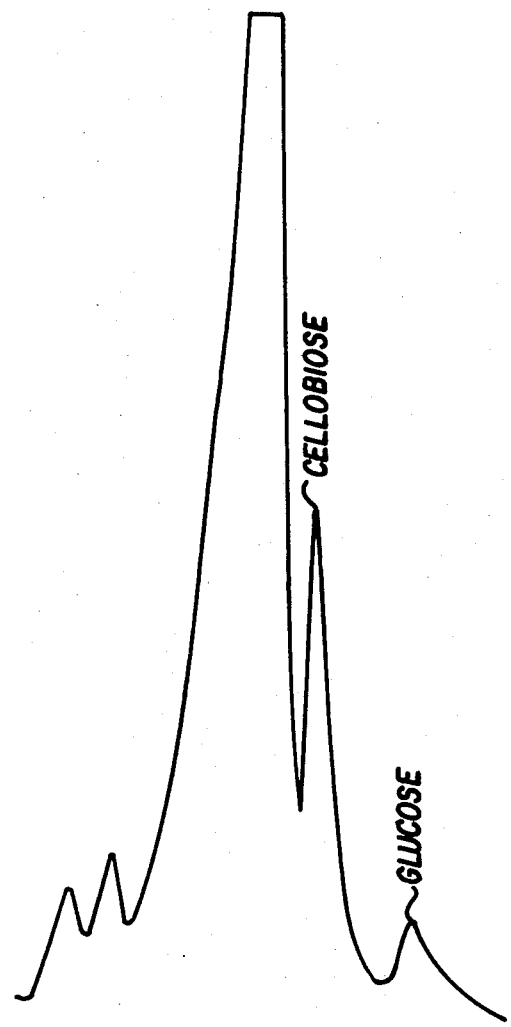
FIG. 8 SACCHARIFICATION BY ENZYME OF GE STRAIN YX H/P MEDIUM, WHOLE CULTURE, 72 HOURS AT 55°C

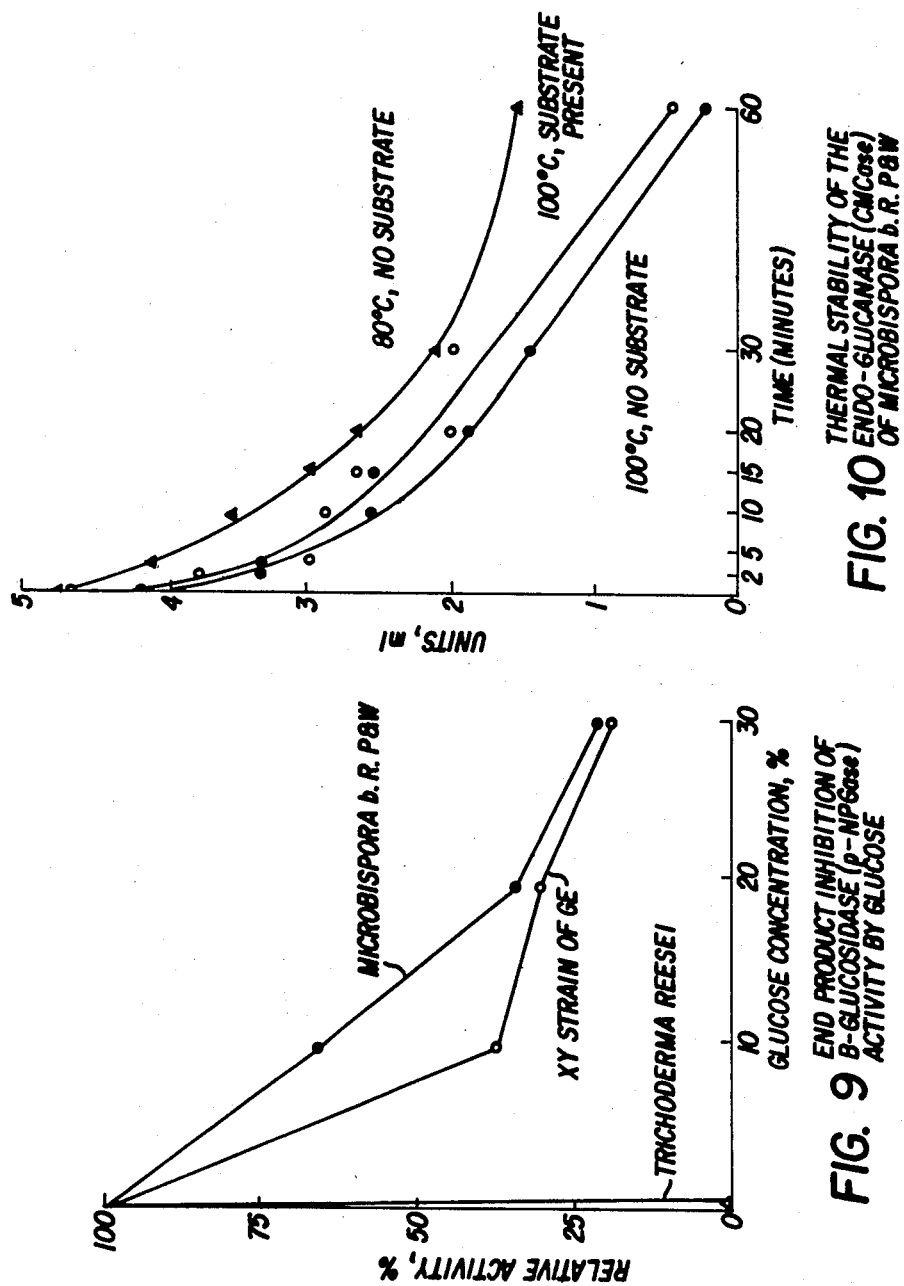
FIG. 9 END PRODUCT INHIBITION OF β-GLUCOSIDASE (β-NPGase) ACTIVITY BY GLUCOSE
FIG. 10 THERMAL STABILITY OF THE ENDO-β-GLUCANASE (CMCase) OF MICROBISPORA b.R. P&W

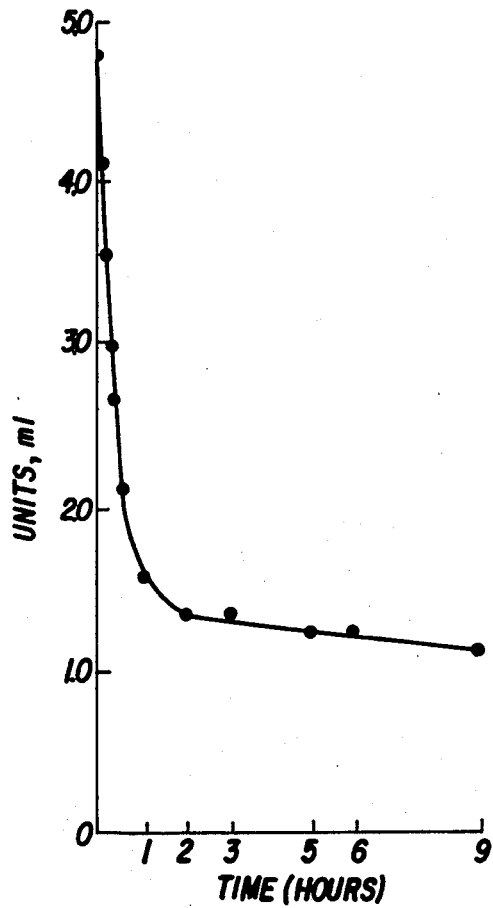
FIG. 11 THERMAL STABILITY OF ENDO-GLUCANASE (CMCase) OF MICROBISPORA b. R. P&W AT 80°C
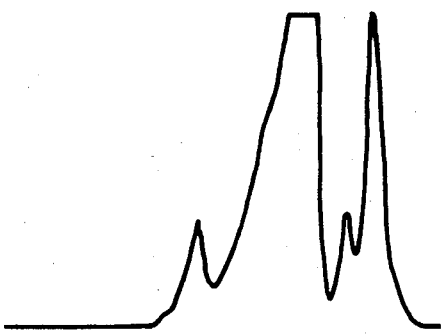
FIG. 12 HPLC PLOT OF TYPICAL SACCHARIFICATION OF P&W PULP BY ENZYME OF M. b. R. P&W GLUCOSE IS THE ONLY SUGAR NOTED 95% OF TOTAL REDUCING SUGAR

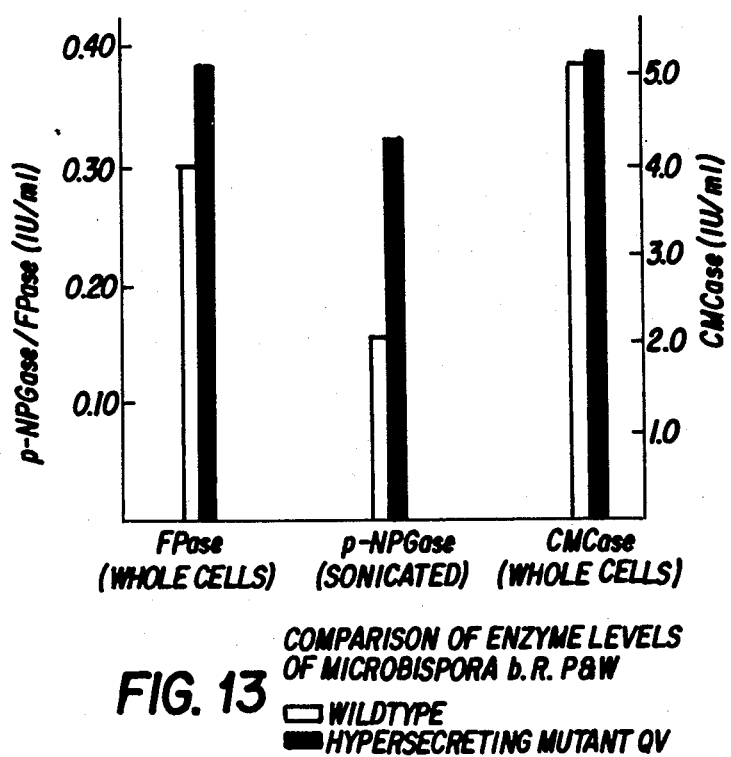
FIG. 13 COMPARISON OF ENZYME LEVELS OF MICROBISPORA b.R. P&W
☐ WILDTYPE
■ HYPERSECRETING MUTANT QV

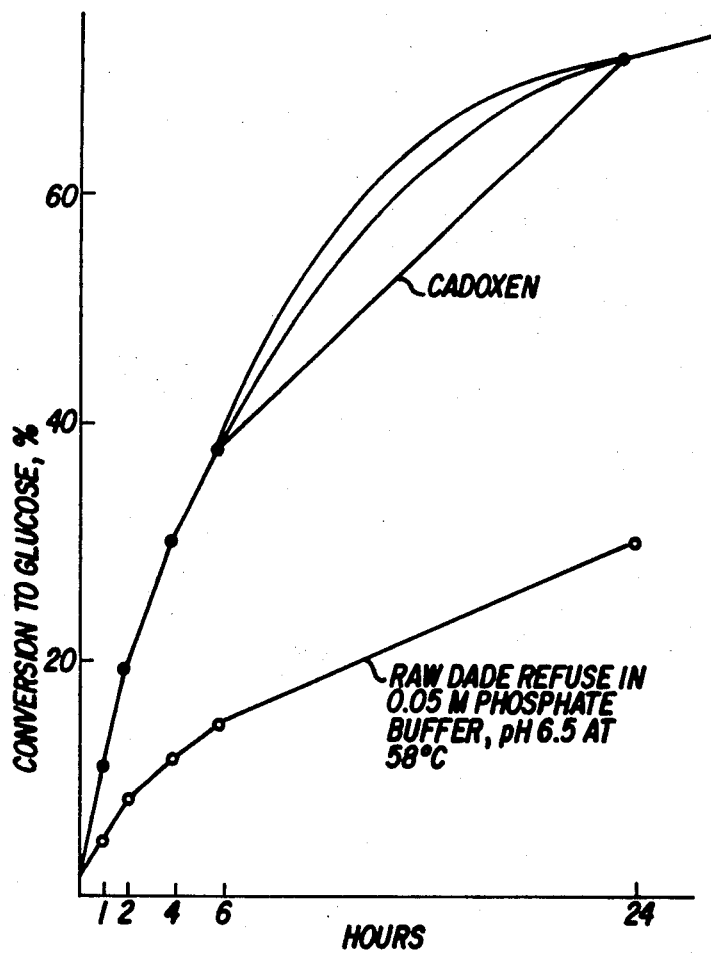
FIG. 14 EFFECT OF PRETREATMENT ON SACCHARIFICATION OF DADE COUNTY MUNICIPAL REFUSE BY MICROBISPORA b. R. P&W MUTANT QV

METHOD FOR THE CONVERSION OF A CELLULOSIC SUBSTRATE TO GLUCOSE USING *MICROBISPORA BISPORA*, STRAIN RUTGERS P&W

BACKGROUND OF THE INVENTION

The present invention relates to a process for the enzymatic saccharification of a cellulosic substrate to glucose by hydrolyzing it with cellulose enzymes from the microorganism *Microbispora bispora*, Rutgers P&W (M.b.R.) or a mutant thereof.

Cellulose is said to be the most widely occurring organic compound on earth. It is composed essentially of repeating subunits of D-glucose, linked by $\beta$-(1-4)-glycosidic bonds. Total hydrolysis yields D-glucose, and partial hydrolysis gives the disaccharide cellobiose, which is $\beta$-D-glucopyranosyl-$\beta$-(1-4)-D-glycopyranose. Therefore, cellulose is a $\beta$-1,4-glucan.

Cellulose constitutes the major storage form of photosynthesized glucose and the major component of solar energy which has converted to biomass. As worldwide demand for energy and food supplies increases, cellulose in its abundance becomes an attractive raw material for supplying these needs. The glucose subunits of cellulose can be used in a variety of processes for production of energy on the one hand or for use in the production of protein on the other.

A major impediment to cellulose utilization technology, however, has been the difficulty of obtaining glucose in reasonable yield from cellulose while expending reasonable costs in terms of energy input, equipment requirements and the like. Chemical hydrolysis suffers from the drawbacks of high costs of capital equipment, of high processing costs, low yields, production of complex product mixtures and inability to stop the degradation of cellulose at a point which produces primarily the desired product, glucose. Therefore, enzyme-catalyzed saccharification of cellulose is seen as a promising alternative to chemical degradation which can achieve a high efficiency conversion of cellulose to glucose.

Although by tradition, cellulolytic microorganisms are a bane to the pulp and paper industry, causing significant loss through rotting, staining and slime formation, microbial enzymatic decomposition can also be turned to industrial advantage, in the controlled conversion of biomass to ethanol, chemical feedstocks and food. Enzymatic conversion of cellulose to glucose using an enzyme such as cellulase is superior to chemical dissolution in that it proceeds at moderate temperature and pressure, provides recyclable catalysts and frees the environment from the undesirable side products associated with chemical hydrolysis. However, the production of adequate amounts of enzymes such as cellulase is dependent upon identifying a suitable source of substantial quantities of cellulase enzymes in a reasonably pure state.

Cellulase is in actuality a complex of enzymes which act cooperatively, or synergistically, in degrading crystalline cellulose. These enzymes are endo-glucanase, cellobiohydrolase or glucohydrolase, and cellobiase ($\beta$-glucosidase). Current thinking is that a cellulosic substrate is initially hydrolyzed by endoglucanases yielding oligomeric intermediates. These oligomeric intermediates are immediately acted upon by exo-splitting glucanases such as glucohydrolase or cellobiohydrolase to produce, respectively, glucose or cellobiose from the non-reducing termini. Both types of glucanases continue to hydrolyze the residual oligomers, and finally cellobiase cleaves the short chain oligomers and cellobiose to yield glucose. It has been found that the most effective cellulases contain both exo- and endo-splitting components, and only those cellulases containing both are able to produce high saccharification conversions of crystalline cellulose. The simultaneous production of both of these types of enzymes by microorganisms appears to be relatively restricted; good yields have been reported to be obtained from only a few fungal genera, including Fusarium, Penicillium, Phanaerochaete (syn. Sporotrichum) and Trichoderma.

The microorganisms of the *Trichoderma reesei* (*T. reesei*) species are considered in the art to be the best source of all enzymes in the cellulase complex. However the utility of *T. reesei* as a cellulase source is hampered by catabolite repression in the synthesis of cellulase; by inactivity of the cellulase at elevated temperatures; and most importantly, by end-product inhibition during saccharification (cellobiose being in *T. reesei* a strong end-product inhibitor of both endo-glucanase and cellobiohydrolase, with glucose a competitive inhibitor of $\beta$-glucosidase).

Accordingly, the isolation and development of a microbial cellulase source wherein the enzyme product is both resistant to end product inhibition and substantially unimpaired at elevated temperature, is of particular industrial interest, and would constitute a significant advance over the art.

SUMMARY OF THE INVENTION

Accordingly, an object of this invention is to isolate and culture a thermophilic microbial strain capable of manufacturing glucose by the use of a cellulase which is resistant to end-product inhibition. Other objects of the invention include purification of the cellulase produced by such a microbe; initiation of saccharification of cellulosic substrate by the microbe's cellulase; and determination of the rate of the microbe's cellulase production under certain conditions. Yet another object of the invention is to determine the effect on efficiency of glucose production of varying enzyme concentration, substrate concentration, substrate composition, and substrate pre-degradation.

These and other objects are achieved by the invention which is directed to a biological method for the conversion of cellulose to glucose. According to this method, an aqueous medium containing a cellulosic substrate is inoculated with the cellulose-producing microorganism *Microbispora bispora*, strain Rutgers P&W (hereinafter M.b.R.) or its cellulase-producing mutants to produce an inoculated medium. This medium is then maintained under appropriate conditions of temperature and pH such that spurious microorganism growth is prevented and advantage is taken of the M.b.R. ability to thrive at relatively high temperatures. The fermentation of cellulosic substrate produced in this manner is carried out until at least some of the substrate is converted to glucose.

Preferably the conversion may be carried out using the cellulose enzyme complex isolated from M.b.R. or its mutants since this avoids consumption of substantially all of the glucose product by the microorganism. Here, a culture of M.b.R. or its mutant is grown in sufficient quantity to produce the desired amount of cellulase complex. The first two enzymes of the complex are collected as cellular secretion products by directly filtering and collecting the culture broth and by washing the residual mycelium. Then, after the quantity of secreted enzymes is determined to be sufficient, the cells are lysed, sonicated or otherwise ruptured to expel the third enzyme (β-glucosidase) which is membrane bound. The removal of cellular constituents, the recombination of the enzymes to make the complex, and application of the cellulase complex to a cellulose substrate with yield glucose.

It has been found that the hydrolysis of cellulosic substrate with enzymes produced by a culture of M.b.R. or its mutants either in vitro can be accomplished in an aqueous medium even containing as much as about a 35% wt/wt concentration of glucose. A preferred aqueous medium in this regard will finally contain glucose within a weight percent range of from about 5% to 25%.

Preferred hydrolysis conditions include use of temperature of from about 45° C. to about 85° C. and a pH from about 5.5 to about 7.5. An especially preferred fermentation temperature range is from about 50° C. to about 60° C.

A preferred hydrolysis rate for production of glucose is the conversion of at least about 80 percent of the cellulosic substrate to a combination of glucose and cellobiose over a period of about 2 to 24 hr. An especially preferred proportional hydrolysis rate provides conversion of at least about 90% of the substrate to a combination of glucose sand cellobiose with the glucose to cellobiose molar ratio being at least about 2:1, or preferably at least about 5:1. It is especially preferred that at least about 95% by weight of the product mixture is glucose.

Also included within the invention is the cellulase-three enzyme complex isolated from *Microbispora bispora* Rutgers P&W or its cellulase producing mutants. The complex includes endoglucanase, cellobiohydrolase and B-glucosidase with the B-glucosidase being present in an increased amount relative to known cellulase enzyme complexes. The B-glucosidase activity of the cellulase complex of the invention is at least about 0.1 units per ml as assayed using p-nitrophenyl glucoside as a substrate and as derived from 15 ml of cell free sonicate produced from a mature, whole cell, 3 day culture broth. The cellulase enzyme complex of the invention exhibits substantial resistance to end product inhibition (glucose), produces a significantly higher amount of glucose as opposed to cellobiose relative to known cellulase complexes, and has a higher optimum functioning temperature relative to known cellulase complexes. A preferred enzyme complex will exhibit a saccharification activity in a 10% glucose solution of at least about 65% of its activity in a glucose-free solution. An especially preferred enzyme complex will exhibit a saccharification activity in a 20% glucose solution of at least about 30% to 35% of its activity in a glucose-free solution.

The invention further includes the isolated, purified culture of cellulase-producing *Microbispora bispora* Rutgers P&W and its cellulase-producing mutants. The M.b.R. and mutants are characterized by their ability to grow optimally at a temperature of about 58° C.; by their cellulolytic activity to produce primarily glucose; by their substantial resistance to end product inhibition of their cellulose saccharification ability; by their morphological features including bisporulation, filamentary vegetative mycelia, and an appearance which is white to off-white in color; and by their physiological and biochemical features including no reduction of nitrate to nitrite, no starch hydrolysis, and utilization of glucose, rhamnose and inositol but no glycerol or arabinose utilization. The mutants, in turn, are selected for attributes of enhanced cellulase production, cf. M.b.R. Q.V.

BRIEF DESCRIPTION OF THE FIGURES

FIG. 1 shows a picture of a growing colony of M.b.R. and and a close-up thereof.

FIG. 2 shows the profile of endo-glucanase production by M.b.R. in several media.

FIG. 3 shows the profile of β-glucosidase production by M.b.R. in several media.

FIG. 4 shows the effect of the cellulose source on the production of endo-glucanase by M.b.R.

FIG. 5 shows the effect of the cellulose source on the production of β-glucosidase by M.b.R.

FIG. 6 shows the effect of cellulose concentration on the production of β-glucosidase by M.b.R.

FIG. 7 shows an HPLC trace of the products and their relative amounts produced by saccharification of shredded newspaper by the M.b.R. enzyme complex.

FIG. 8 shows on HPLC trace of the products and their relative amounts produced by saccharification of shredded newspaper by the cellulase enzyme complex from GE Strain YX.

FIG. 9 shows the comparative end-product inhibition of β-glucosidase activity of M.b.R., YX strain and *T. reesei*.

FIGS. 10 and 11 show the thermal stability of endogluconase of M.b.R. under various conditions.

FIG. 12 shows an HPLC trace of the saccharification products from M.b.R. enzyme fermentation with P&W pulp.

FIG. 13 shows a comparison of the cellulase enzyme levels produced by M.b.R. and its QV mutant.

FIG. 14 shows the effect of pretreatment upon M.b.R. mutant QV fermentation of municipal refuse.

DETAILED DESCRIPTION OF THE INVENTION

Figure 15:
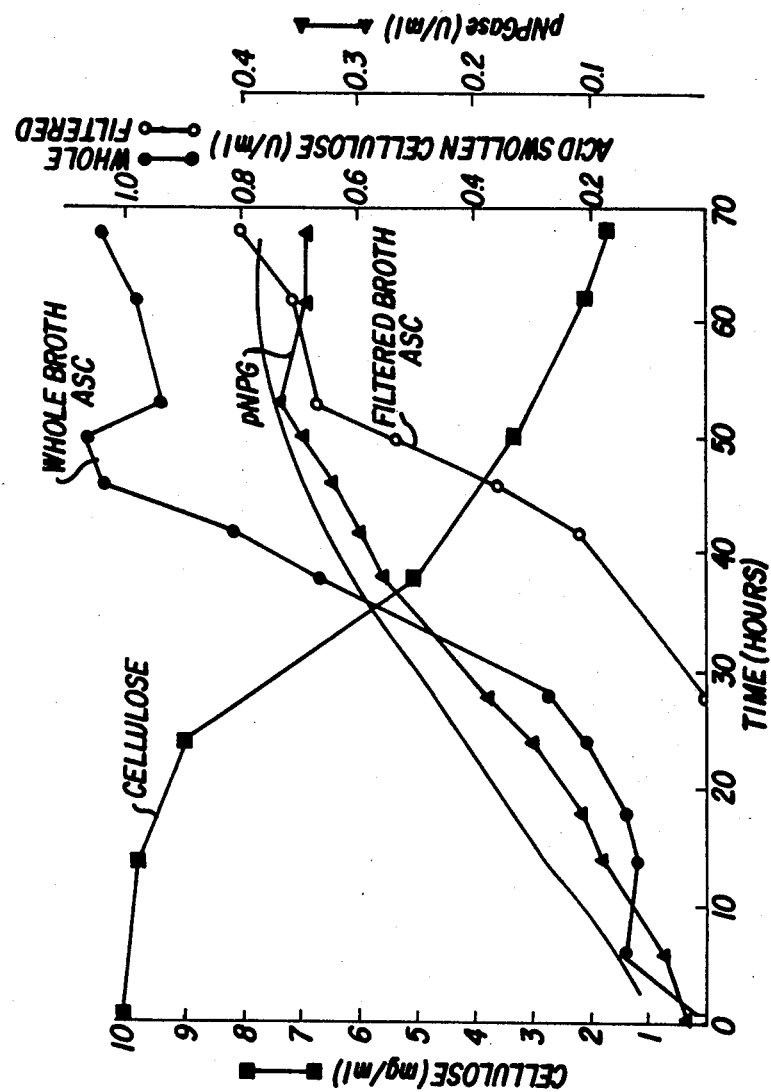
FIG. 15 shows a profile of the 7L. fermentor production of cellulase by M.b.R.

In the following description, the isolation, purification and properties of the M.b.R. strain and its use in a method for conversion of cellulose to glucose are discussed. Functional parameters, process variables and comparative tests are explained in terms of the microorganism's unique properties.

Isolation and Screening of Cellulolytic Thermophilic Actinomycetes of Which M.b.R. is a Member Forty strains of thermophilic actinomycetes were isolated from thermal soils or other sources in some twenty-nine locations in four countries—the United States, New Zealand, China and the West Indies. Soil samples together with hay or microcrystalline cellulose (as the cellulose source) were incubated in flasks at 60° C. and maintained in "just-moist" condition. The growth of cellulose digesting actinomycetes was much favored, to the extent that the colonies were visible to the naked eye as dry, powdery zones on the substrate surface. Plating followed on Tabata-Terui medium (defined in Table II) containing cellulose (1% Avicel PH-105) as the sole carbon source. Novobiocin and crystal violet were added in varying concentrations to aid in the suppression of contaminating bacterial species. The plates were incubated in a Hotpack temperature/humidity controlled incubator maintained at a 90–95% humidity level. It was possible to sustain incubation without dehydration for an extended period up to six weeks.

The strains were then innoculated into liquid shake flask cultures of Hagerdal/Ferchak/Pye (defined in Table I) medium with 1% Avicel (micro-crystalline cellulose) as the substrate. Only eleven of the original forty strains were successfully grown in liquid culture.

Of the eleven strains, the strain later identified as M.b.R. was one of two actinomycete strains which showed good cellulolytic activity in the liquid culture. They were able to completely utilize the 1% cellulose suspension within 72 hours. The second strain was ultimately rejected owing to its instability of growth in liquid culture.

The strain M.b.R. is a member of the species *Microbispora bispora* but in contrast with other members of this species, this strain shows pronounced cellulolytic activity and substantial resistance to end product inhibition of this activity. M.b.R. has been placed on deposit with the U.S.D.A. culture collection depository at Peoria, Ill. It has been given NRRL No. 15568.

Biological Evaluation of M.b.R.

There are six basic tests which illustrate the unique growth properties of M.b.R. These are:
(1) Growth on solid media (Hagerdal/Pye medium, Table I and Tabata/Terui medium, Table II),
(2) Growth in liquid culture,
(3) Saccharification efficiency,
(4) Resistance to end-product inhibition,
(5) Thermal stability of the enzymes produced,
(6) Stability of the strain in continued culture.
The behavior of M.b.R. and of some comparative microorganisms in each of these six tests is as follows.

Test (1) Growth on solid media:

For the growth determinations, a solid medium consisting of Tabata/Terui salts with cellulose (see Table 1) was used. Cellulolytic activity was indicated by the formation of discrete zones of cellulose clearing surrounding the colonies. For these primary tests, 1% Avicel PH-105 as the cellulose source was used but it was found that often three weeks growth were required for appearance of the clearing zones. A second, more rapid system for growth screening of large numbers of samples is use of Tabata/Terui salts with 0.5% acid swollen cellulose. Excellent clearing zone formation by M.b.R. was obtained in a period of only 3–7 days. This test shows that the microorganism has the ability to digest and thrive upon cellulose as its sole source of carbon and to secret cellulose. Growing colonies of M.b.R. in the second medium and a close up picture of the colonies are shown in FIG. 1.

TABLE I
HAGERDAL/PYE MEDIUM

| | |
|---|---|
| 1.5 gm | NaCl |
| 3.1 gm | $(NH_4)_2SO_4$ |
| 9.1 gm | $Na_2HPO_4$ |
| 0.9 gm | $KH_2PO_4$ |
| 50.0 mg | NaEDTA |
| 200.0 mg | $MgSO_4.7H_2O$ |
| 8.0 mg | $ZnSO_4.7H_2O$ |
| 20.0 mg | $FeSO_4.7H_2O$ |
| 15.2 mg | $MnSO_4.H_2O$ |
| 20.0 mg | $CaCl_2$ |
| 1.0 mg | Biotin* |
| 1.0 mg | Thiamine HCl* |
| 1.0 gm | Yeast Extract |

TABLE I-continued
HAGERDAL/PYE MEDIUM

| | |
|---|---|
| 10.0 gm | Cellulose (AVICEL PH-105) |
| $H_2O$ - q.s. | 1 liter |

*Vitamins are filter sterilized and added after autoclaving N.B. - vitamins and yeast extract are not required by *M. bispora*.

TABLE II
TABATA/TERUI MEDIUM (modified)

| | |
|---|---|
| 10.0 gm | Cellulose (AVICEL PH-105) |
| 2.0 gm | $K_2HPO_4$ |
| 0.5 gm | KCl |
| 1.0 gm | $MgSO_4.7H_2O$ |
| 0.5 gm | NaCl |
| 1.0 gm | $NH_4NO_3$ |
| 1.0 gm | Proteose Peptone |
| 1.0 gm | $CaCl_2.2H_2O$ |
| 0.5 gm | Yeast Extract |

FOR ISOLATION PLATES:
a. Reduce Cellulose to 2.0 gm/l
b. Omit Peptone
c. Reduce $CaCl_2$ to 0.1 gm/l
d. Add Agar - 20 gm/l

FOR SELECTION OF MUTANTS WITH ENHANCED - GLUCOSIDASE PRODUCTION:

As for "Isolation Plates" but,
a. replace Avicel with 0.5% acid swollen cellulose, or cellobiose,
b. add 0.5% (w/v) 2-deoxyglucose as catabolite repressor Test (2) Growth in Liquid Culture:

Growth in liquid culture (e.g. shake flask) is important for the production of enzyme both for commercial use and for laboratory study. Several of the cellulolytic actinomycetes isolated were rejected for further study on the basis of their inability to grow in liquid culture.

Actinomycete M.b.R. grows rapidly in liquid culture and produces very respectable levels of enzyme. Enzyme production is directly related to the culture conditions. Thus, for example, the medium of Hagerdal/Pye (Table I) gave increased yield of both endo-glucanase and β-glucosidase over the Tabata/Terui medium (Table II) (see FIGS. 2 and 3 respectively for this profile). Enzyme production, specifically the production of endoglucanase and β-glucosidase, is also affected by both the nature (see FIGS. 4 and 5 for this profile) and by the concentration (see FIG. 6 for this profile) of the cellulosic substrate. Other factors affecting enzyme production include (a) the pH, which increases enzyme production when the H/P medium is used at pH of 7.2 instead of 6.6, (b) nitrogen source, ammonia nitrogen gives much higher enzyme levels than does nitrate nitrogen, (c) and temperature, slightly higher enzyme levels are reached at 60° than at 55° C. and both growth and enzyme production are poor at 43° C. Finally, there is some indication that enzyme production may be boosted by the addition of certain nutrients such as galactose to the culture medium. There is no need for the vitamin supplements (thiamine and biotin) recommended by the Pye medium, and this results in a less expensive medium.

Test (3) Saccharification efficiency:

Ultimately the practical value of the enzyme produced will be determined by its saccharification efficiency against readily available substrates. A realistic goal from this standpoint, is to produce a 20% glucose syrup for use as a chemical feedstock.

A comparison was made of the cellulose saccharification by enzymes from M.b.R's and G.E.'s YX strains using shredded NY Times newspaper (see Table 3 for the newspaper analysis). The microorganism G.E.YX is a thermophilic actinomycete discovered by the General Electric Company. The enzyme preparation derived from it was received from Lehigh University. High Performance Liquid Chromatography (HPLC), the analytical details of which are given in the examples section, was used to separate the saccharification products. The HPLC traces of the product mixture are given in FIGS. 7 (M.b.R.) and 8 (G.E., XY). It will be noted that M.b.R. produces 6 times more glucose than a comparable level of YX enzyme. The enzyme of the G.E. YX strain in these tests produces cellobiose almost exclusively.

In current practical terms the YX enzyme yields only 2% glucose plus 12% cellobiose. This cellobiose still has to be converted to glucose and requires the addition of supplemental β-glucosidase from another source at extra cost.

The HPLC studies also show that M.b.R. possesses a xylanase when grown on Avicel PH 105 (YX does not). Xylans are of commercial interest as chemical feedstocks since they are major components of biomass.

In these laboratory tests a saccharification efficiency for M.b.R. of 18% has been achieved which is an excellent result since it shows the enzyme acting at 99% efficiency.

TABLE III

| PROXIMATE ANALYSIS OF CELLULOSIC SUBSTRATES (Percent of Dry Weight) | |
| --- | --- |
| | N.Y. Times |
| Ash (550° C.) | 0.46 |
| Cellulose* | 45 |
| Lignin, Hemicellulose, Xylosans & Non-Specified | 54.54 |
| TOTAL | 100 |

*Cellulose by Method of Updegraff, D.M., Analyt. Biochem. 32:420 (1969)

Test (4) Resistance to end-product inhibition:

The production of a 20% glucose syrup means, of necessity, that the β-glucosidase enzyme must be capable of acting in the presence of 20% glucose. The resistance to end-product inhibition of M.b.R., YX, and Trichoderma enzymes are compared in FIG. 9. It will be noted immediately that the glucosidase of Trichoderma is totally inhibited by a concentration of less than 1%. M.b.R. enzyme, on the other hand, retains 65% of its activity in a 10% glucose syrup compared to only 37% for YX. M.b.R. enzyme still retains 34% of its activity in 20% glucose and even 21% activity in a 30% syrup. These are outstanding values.

Test (5) Thermal stability of the enzymes produced:

As enzymatic hydrolysis of cellulose is basically a chemical reaction; the rate of conversion is directly related to the temperature at which the saccharification is carried out. 60° C. was used which is a high temperature for biological systems. For continued reaction, enzyme stability at these high temperatures is also important. The M.b.R. endoglucanase is stable for weeks at 60° C. and at 80° C. retains 55% of its activity after 20 minutes and 23% of its activity after 9 hours at this temperature. Even at 100° C., more than 50% of its original activity is maintained after 15 minutes (see FIGS. 10 and 11). The β-glucosidase, while considerably more heat labile, is still active after 48 hours at 55° C.

Test (6) Stability of the strain in continued culture:

A major problem with certain thermophilic actinomycetes has been their tendency to lose viability after continued culture. Obviously, it is essential, for commercial purposes, to have an organism that will retain both its viability and its ability to produce enzyme after repeated culture. Several of the original isolates were rejected because they lacked this potential.

M.b.R. has proved itself to be a throughly stable organism after more than 11 months of continued culture. The organism can also be stored easily in liquid nitrogen and in soil and on agar slants. Its viability after storage in liquid nitrogen after 1½ months was tested and there was no loss of viability and immediate growth occurred. The organism has also been recovered from slants after storage for over 6 months and likewise from soil. The most rapid recovery is from liquid nitrogen and this would certainly be the storage method of choice.

The performance of strain M.b.R. when considered by these six criteria shows that it is highly efficient for cellulose conversion. The organism is stable; it grows well on both solid and liquid media; and possesses an enzyme system that is thermo-stable, resistant to end-product inhibition, and, additionally, has a wide pH latitude. The enzyme system has demonstrated its superiority and potential in saccharification studies.

Generally, the production and activity of the enzyme complex by M.b.R. is characterized by a high rate of production of each of the three enzymes of the complex. Specifically, the enzyme properties of M.b.R. have been found to depend upon the high amount of β-glucosidase produced.

Enzyme Characterization of the M.b.R. System

The cellulase complex of *M. bispora* Rutgers P&W generally is characterized as having optimal proportions of the third component β-glucosidase. It is present as a cell bound enzyme rather than secreted as are the first two components.

In specific terms, the β-glucosidase enzyme of M.b.R. is the most important of the three components of cellulase since its proportions affects saccharification efficiency and the ultimate production of glucose.

Thus, for effective saccharification of cellulosic substrates the various components of the enzyme complex should be present in such proportions that the activity of the entire complex is optimized. Since it has been noted in the cellulases of both Trichoderma and Thermomonospora (Penn/G.E. strain YX) that the β-glucosidase is the limiting enzyme of this component in M.b.R. has been investigated and it has been found that, unlike commercial Trichoderma enzyme and also Thermomonospora, M.b.R. has an ample supply of β-glucosidase compared to the other enzymes of the cellulase complex (see Table IV for the details of the effect of the M.b.R. glucosidase concentration upon saccharification). It was found that although additional β-glucosidase increase glucose production, it does not increase the saccharification efficiency of M.b.R. since the effect is not linear.

TABLE IV

| Effect of β-Glucosidase Level on Saccharification of Avicel by *Microbispora bispora* R. P & W cellulase + | | | | | |
| --- | --- | --- | --- | --- | --- |
| β-Glucosidase | Glucose Level (mg/ml) | | | | Total Saccharides |
| (units/ml) | 1 hr. | 3 hr. | 6 hr. | 24 hr. | mg/ml (24 hr.) |
| 0.006 | 0.07 | 0.21 | 0.41 | 1.38 | 2.30 |
| 0.04 | 0.31 | 0.78 | 1.29 | 3.72 | 4.30 |

TABLE IV-continued
Effect of β-Glucosidase Level on Saccharification of
Avicel by *Microbispora bispora* R. P & W cellulase +

| β-Glucosidase | Glucose Level (mg/ml) | | | | Total Saccharides |
|---|---|---|---|---|---|
| 0.11* | 0.42 | 0.93 | 1.52 | 4.23 | 5.10 |
| 0.23 | 0.46 | 0.99 | 1.59 | 4.26 | 5.70 |

*N.B. 0.11 units/ml is the equivalent cellulase concentration from a whole cell suspension. Doubling this level does not significantly increase the saccarification efficiency. At this level, glucose accounts for 83% of the saccharification products.
+ Each reaction mixture contained 15 ml of culture supernatant (-glucosidase free) + sufficient concentrated -glucosidase (from sonicated cells) to provide the specified levels and $PO_4$ buffer to 25 ml total. Avicel PH101 0.25 gm was added to each flask to give a cellulose concentration of 10 mg/ml.

Location of M.b.R. β-Glucosidase

Additionally, the loction of the β-glucosidase enzyme in M.b.R. has been investigated. As in Trichoderma and Thermomonospora, the β-glucosidase activity of M.b.R. is cell associated (cell-bound). The enzyme is readily released following sonic disruption of the cells. The apparent activity of the enzyme is increased 45% by this procedure (See Tables V&VI).

TABLE V
Release of β-Glucosidase by Sonication Fractionation

| Fraction measured | β-Glucosidase activity iu/ml |
|---|---|
| Washed cells | 0.11 |
| Sonicate Supernatant | 0.12 |
| Sonicate Debris | 0.01 |

Cells were washed twice with 50 mM $PO_4$ Buffer, pH 6.5, resuspended in same buffer and sonicated 2 minutes with micro-tip (30 seconds sonicate, 1 minute cooling - repeat 5 times). β-Glucosidase was assayed by the p-NPG method.

TABLE VI
The Effect on Saccharification of Solubilized β-Glucosidase

| Enzyme Prep. | Saccharification Efficiency Glucose mg/ml/24 hours |
|---|---|
| Whole Cells | 2.92 |
| Sonicated (cell free) | 4.23 |
| Avicel PH 101,55° C., pH 6.5 $PO_4$ Buffer. | Whole Cell |

Preparation contained 15 ml culture broth, 10 ml buffer, 11.5 mg/ml Avicel. Sonicated preparation contained 15 ml of cell free sonicate, buffer and Avicel as above.

The location of β-glucosidase was determined by separating the extra-cellular fluid and then breaking the cells and fractionating into the cell wall and cell sap fractions. No β-glucosidase was found in the extracellular broth. By sonic disruption of the cells and subsequent ultra-centrifugation, the β-glucosidase is seen to remain soluble and is not tightly bound to the cell wall or cell membrane. Thus, it is either intracellular or periplasmic (between the cell wall and membrane) or loosely membrane bound.

Saccharification of Crude Cellulosic Substrates

M.b.R. efficiently saccharifies cellulosic substrates over a short period of time to produce primarily glucose. To demonstrate this utility, the saccharification of "Cetus" Baltimore municipal air-classified waste, "Dade County" municipal garbage, Avicel PH 101 (purified, fairly crystalline, cellulose) and P & W pulp (a much less crystalline cellulose) have been examined. Cellulose analyses were made of these substrates (Table VII) and a comparison of their saccharification by M.b.R. is presented in Table VIII. The conditions for saccharification are given with Table VIII. All substrates were milled through the fine screen (0.1 mm pore) of a Wiley mill before analysis or saccharification.

TABLE VII
Cellulose Content of Cellulosic Substrates*

| Substrate | Cellulose % |
|---|---|
| Avicel 101 | 96 |
| P & W Pulp | 85 |
| Cetus Baltimore Municipal Waste | 45 |
| Dade Garbage | 40 |

*by Updegraff method, see Table III.

TABLE VIII
Saccharification of Cellulosic Substrates by M.b.R. Cellulase

| Substrate | FPase (U/ml) | Cellulose (mg/ml) | Glucose (mg/ml/ 24 hr) | Efficiency % Conversion |
|---|---|---|---|---|
| Avicel 101 | 0.12 | 11.5 | 2.92 | 25.4 |
| P & W Pulp | 0.12 | 10.2 | 3.85 | 37.7 |
| Cetus Baltimore Municipal Waste | 0.12 | 10.8 | 2.03 | 18.8 |
| Dade Garbage | 0.12 | 9.6 | 1.85 | 19.3 |

The saccharifications were preformed using crude enzyme (whole cell cultures) at 55° C. in pH 6.5 phosphate buffer. The preparations contained 15 ml of culture broth, 10 ml $PO_4$ buffer and sufficient 0.3 gm of each of Avicel and P & W Pulp,0.6 gm each of Dade and Cetus Baltimore Municipal Materials.

Variables in the Enzymatic Saccharification of Cellulose Using M.b.R.

Saccharification of Cellulosic Substrates by Crude Microbial Cellulase from *Microbispora bispora* Rutgers P&W The practical value of *Microbispora bispora* Rutgers P&W will ultimately be determined by its saccharification efficiency against readily available substrates. Compared to GE's YX strain and a cell free filtrate of Rutger's C-30 strain of *Trichoderma reesei*, M.b.R. enzyme produces a high level of glucose while YX and C-30 produce cellobiose almost exclusively. Since cellobiose would have to be converted to glucose by the use of supplemental β-glucosidase at additional cost, the ability of M.b.R. to produce glucose directly is a major advantage of this organism.

Saccharification efficiencies for M.b.R. have been found to be at least 16% in terms of available cellulose converted to glucose in 48 hours. Using P&W pulp as a substrate, an efficiency of 52.3% in only 24 hours and up to 95% of the total reducing sugar produced is glucose has been achieved (See FIG. 12 for an HPLC trace of this product mixture).

Effect of enzyme concentration on saccharification

As would be expected, higher levels of enzyme give a higher yield of glucose Table IX summarizes the data obtained from the study of this effect.

TABLE IX
Enzyme concentration in relation to saccharification

| FPase IU* | Total RS mg/dl | Glucose mg/dl | Glucose % total | Glucose mg/unit | Conversion** % to glucose |
|---|---|---|---|---|---|
| 4.4 | 360 | 317 | 88 | 72.0 | 31.7 |
| 8.8 | 480 | 458 | 95 | 52.0 | 45.8 |
| 13.2 | 680 | 523 | 77 | 39.6 | 52.3 |

Saccharification of P & W pulp by M.b.R. for 24 hours at 58° C. in pH 6.5 phosphate buffer. 1.18 gm pulp/dl = 1 gm (1%) cellulose.
*Filter Paper-ase units - 20 ml whole culture (0.22 I.U./ml) = 4.4 I.U.
**Saccharification efficiency in terms of % conversion of cellulose to glucose.

Thus, by trebling the enzyme level the total saccharification can be increased from 31.7% to 52.3% over 24 hours. There is, however, a marked decrease in the amount of glucose produced per unit enzyme. The conversion of cellulose to glucose can be enhanced by the use of additional enzyme but the increase is not proportional to the amount of enzyme added, a doubling of the enzyme giving only a 44.5% increase in glucose produced.

Effect of substrate concentration on saccharification

Increasing the amount of substrate available increases the amount of glucose produced. Table X summarizes the data obtained from a study of this effect.

TABLE X

Substrate concentration in relation to saccharification

| Cellulose mg/dl | Glucose mg/dl 24 hours | *Conversion % 24 hrs | Glucose mg/dl 96 hours | *Conversion % 96 hrs |
|---|---|---|---|---|
| 500 | 236 | 47.2 | 333 | 66.7 |
| 1000 | 350 | 35.0 | 555 | 55.5 |
| 2000 | 442 | 22.1 | 590 | 29.5 |

Saccharification of P & W pulp by M.b.R., 8.0 I.U. FPase activity (40 ml whole culture, 0.20 I.U./ml = 8.0 I.U.) at 58°, pH 6.5 buffer.
*Saccharification efficiency in terms of % conversion of cellulose to glucose.

As with enzyme concentration, however, this effect is not proportional to the amount of substrate present. Thus, in a 24 hour period, doubling the substrate from 0.5% to 1% cellulose increased the amount of glucose by only 48%. Doubling the substrate again to 2% cellulose gave an additional increase in glucose of only 26%.

Effect of substrate composition on saccharification

Various cellulose sources vary as to their particle size and degree of crystallinity and, hence, as to their degree of resistance to attack by the cellulase enzyme complex. In addition to P&W pulp, it was decided to adopt the New York Times newspaper as a "standard" saccharification substrate. The Times secures its newsprint from a number of sources and, hence, no particular issue can really be considered "standard". Several samples of the Times clean newsprint were obtained including a reprocessed paper from Garden State Paper and two virgin pulps from Canadian manufacturers, Spruce Falls and Abitibi/Chandler.

These newsprints, together with N.Y. Times printed paper, P&W pulp and other cellulose sources were compared in saccharification studies and were found to differ markedly. Table XI summarizes the data obtained from this study.

P&W pulp appears to be the most readily degraded cellulose source followed by Solka Floc BW 200 which is a finely ball-milled product consisting of 25% kraft pulp and 75% sulfite pulp. Solka Floc SW 40 which is not milled and which consists of 100% sulfite pulp was more difficult to degrade. Of the newsprints, the Abitibi/Chandler was significantly more resistant to attack than Spruce Falls or Garden State reprocessed. The relatively weak saccharification of the printed Times could be due to the presence of the ink or could just as easily be accounted for by the newsprint used (and unknown to us) since it was attacked at the same rate as the Abitibi/Chandler samples.

Mutagenic Variants of M.b.R.

Mutants of M.b.R. may be produced by known methods such as radiation and application of chemical mutagens. It has been found that of these methods chemical mutigens can improve will improve the efficiency of the cellulase complex of M.b.R., as long as they do not cause change in the cellular binding of the third component of the complex. For example, use of the chemical mutagen N-methyl-N-nitro-N-nitrosoguanidine produces several mutants which have activities similar to M.b.R. They may be preserved both on agar slants and also under liquid nitrogen. Some of these mutants denoted as Q1, Q2 and QR through QW are characterized in Table XII, and their enzymes compared to both the original M.b.R. strain and the Penn/GE organism.

Mutant strain QV has been deposited with the U.S.D.A. culture depository and has been given NRRL number 15569.

One of these mutants, original QV, in particular, shows a significant improvement over the wildtype strain (FIG. 13). Both β-glucosidase (pNPGase) and filter paper activity are increased though endoglucanase (CMCase) activity is increased only slightly. This mutant has been tested in saccharification studies against several substrates (Table XIII), and will produce up to 73% efficiency of conversion of cellulose to glucose in 24 hours including a 71% conversion of cadoxen extracted Dade County municipal refuse.

TABLE XII

Comparison of wildtype and mutants M.b.R. with regard to cellulase yield

| | Enzyme Yield (IU/ml) | | |
|---|---|---|---|
| | pNPGase | CMCase | FPase |
| Q (M b.R.)* | 0.17 | 5.11 | 0.30 |
| Q1 | 0.21 | 6.00 | 0.67 |
| Q2 | 0.15 | 4.11 | 0.31 |
| QR | 0.21 | 2.00 | 0.18 |
| QS | 0.12 | 2.88 | 0.23 |
| QT | 0.22 | 4.89 | 0.36 |
| QU | 0.17 | 4.67 | 0.35 |
| QV | 0.22 | 5.33 | 0.38 |
| QW | 0.17 | 5.00 | 0.33 |

TABLE XI

Substrate composition in relation to saccharification

| Substrate Type | Dry Wt. gm | Cellulose gm | Glucose mg/dl 24 hours | *Conversion % 24 hours | Glucose mg/dl 48 hours | *Conversion % 48 hours |
|---|---|---|---|---|---|---|
| 1. P & W Pulp | 1.18 | 1.0 | 395 | 39.5 | 518 | 51.8 |
| 2. New York Times | 2.23 | 1.0 | 115 | 11.5 | 130 | 13.0 |
| 3. Garden State | 2.23 | — | 172 | 17.2 | 208 | 20.8 |
| 4. Spruce Falls | 2.23 | — | 163 | 16.3 | 181 | 18.1 |
| 5. Abitibi/Chandler | 2.23 | — | 119 | 11.9 | 121 | 12.1 |
| 6. Whatman CC-41 | 1.00 | 1.0 | 211 | 21.1 | 302 | 30.2 |
| 7. Solka Floc SW 40 | 1.00 | 1.0 | 242 | 24.2 | 351 | 35.1 |
| 8. Solka Floc BW 200 | 1.00 | 1.0 | 342 | 34.2 | 473 | 47.3 |

Saccharification of substrates by M.b.R., 8.0 I.U. FPase activity (40 ml whole culture, 0.02 I.U./ml = 8.0 I.U.) at 58° C. in pH 6.5 phosphate buffer.
*Saccharification efficiency in terms of % conversion of cellulose to glucose.

TABLE XII-continued

Comparison of wildtype and mutants M.b.R. with regard to cellulase yield

| | Enzyme Yield (IU/ml) | | |
|---|---|---|---|
| | pNPGase | CMCase | FPase |
| YX (GE)[2] | 0.06 | 5.00 | 0.34 |

[1]Three day whole cell cultures. All assays run at 65° C. in .05 M potassium phosphate buffer pH 6.5. CMC type 7L. Filter paper 1 × 6 cm strips of Whatman #1.
[2]YX (GE) [Equivalent Growth Conditions].
*Original parent

TABLE XIII

Saccharification of cellulosic substrates by M.b.R. mutant QV

| Substrate | Glucose mg/ml 24 Hours | % Conversion To Glucose |
|---|---|---|
| Dade Municipal Refuse (M.R. Control) | 1.50 | 30 |
| Acid Swollen Dade County M.R. | 1.75 | 35 |
| Cadoxen Extract of Dade County M.R. | 3.54 | 71 |
| Whatman CC-41 | 1.57 | 31 |
| Acid Swollen CC-41 | 3.62 | 73 |
| Extracted & Swollen Poplar[1] | 3.51 | 70 |
| P & W Pulp | 2.86 | 57 |

Each reaction mixture contained 15 ml of whole culture broth, sufficient substrate to give 125 mg of cellulose and 0.05 M phosphate buffer pH 6.5 to bring total mixture to 25 ml. Final 25 ml mixture contained 0.22 IU FPase activity/ml and 0.5% cellulose. Saccharification was carried out in stoppered 50 ml flasks on a shaker at 58° C. Glucose concentration at 24 hours was measured using a Y.S.I. glucose analyzer model 27A.

Pretreatment of Cellulosic Substrates

It has long been known that the degradation of cellulosic substrates by microbial enzymes can be enhanced by pretreatment of the cellulose in order to: (1) break down the lignocellulosic structure (delignification), or (2) to render the cellulose less crystalline in structure. A whole host of treatments have been employed, more or less successfully, including such procedures as milling, acid swelling (see Example 2), alkali swelling, alcoholic delignification, cadoxen extraction (see Example 2), irradiation, steam explosion, etc. In general, all of these methods are effective for increasing the glucose yield according to the invention. Three methods have been examined as illustrative methods:
(1) Acid swelling using 85% phosphoric acid
(2) Delignification using concentrated acetic and nitric acids,
(3) Cadoxen extraction.

While Dade County municipal refuse is 40% cellulose, this cellulose was found to be resistant to the action of the cellulose of M.b.R. showing only a 19% efficiency of conversion to glucose in 24 hours. Using mutant QV with enhanced cellulolytic ability the saccharification was increased to 30%. In comparison, a cadoxen extract of Dade County refuse yielded a 71% conversion of cellulose to glucose in 24 hours using the enzyme of the mutant strain of M.b.R. FIG. 14 illustrates this effect.

Scale-up Procedures

Fermentation scale up can often pose intractible problems for experimental culture samples. Transient lack of nutrients and essential gases are often multiplied by the large scales of practical production so that fermentation is difficult to maintain. Despite these problems, however, the successful scale-up of the cellulose fermentation of M.b.R. from shake flask to 7 liter fermentor has been achieved. Fermentation broths have been produced that match shake flask cultures in cellulolytic activities and which possess nearly twice the pNPGase (β-glucosidase) activity normally found in flask cultures of M.b.R. (Table XIV). A profile of the fermentation is presented in FIG. 15.

Significant increases in the production of cellulase components may also be derived from the implementation of large scale pH control and from manipulation of cellulose concentration and dissolved oxygen.

TABLE XIV

Comparison of enzyme production by M.b.R. in shake flask and fermentor

| Method of Cultivation | pNPGase* | Acid Swollen Cellulase+ | CMCase+ |
|---|---|---|---|
| Shake Flask | 0.18 | 0.83 | 2.05 |
| Fermentor | 0.34 | 0.80 | 1.96 |

*Whole broth assay
+Supernatant only

The following examples are provided as further illustrations of the invention and of methods for analyzing the enzyme products produced.

EXAMPLE 1

Saccharification of Dade Refuse Using M.b.R.

A 500 ml culture of M.b.R. broth was grown using the Hagerdal/Pye nutrient medium of Table 1. Spores of M.b.R. frozen in liquid nitrogen are slowly warmed to ambient temperatures, then using sterile techniques, they are placed in the nutrient medium, and exposed to sterile air at 50° C. for three days. The culture is then tested for saccharification activity and the grown strain identified as to its morphological and biochemical characteristics. These include bisporulation, filamentary vegetative and aerial mycelia and a white to off-white color as well as no reduction of nitrate to nitrite, no starch hydrolysis and glucose, rhamnose and inositol utilization but not glycerol or arabinose utilization. The culture is stored in the refrigerator until needed.

A sample of Dade County cellulosic refuse is milled to a particle size of about 20 to 100 mesh US sieve series, then combined to yield a 2 percent by weight slurry in water. At the same time a combination of mineral salts containing Mg, Zn, Fe, Mn, Ca, $PO_4$ and $SO_4$ in a concentration equal to those found in the Hagerdal/Pye medium is used to produce an M.b.R. culture from which the cellulase enzyme complex is obtained by cell sonification. Saline is added to adjust the electrolyte balance to physiologic levels microcrystalline cellulose is added as a growth nutrient and ammonium phosphate/sodium phosphate buffer is added to adjust the pH to 6.5 and provide a source of ammonia. The cloudy slurry containing the cellulosic substrate is poured into sterile 7 L. fermenter flasks, sterilzed and then about 100 ml of the cellulose enzyme complex isolated from M.b.R. and having a B-glucosidase activity of about 0.1 units per ml as measued by a p-nitrophenyl glucoside assay (equivalent cellulase concentration from a 3 day whole cell culture broth suspension) may be added to each of the flasks.

For hydrolysis, the flasks containing the cellulase complex may be stoppered with sterile cotton plugs, placed in a warm water shaker bath and shaken at 58° C. for 24 hr. During this time, the flask contents may become clear but also more viscous. Shaking may then be stopped, the flask contents filtered and the solid residue weighed. The filtrates may be analyzed by HPLC methods to determine the complex types and proportions of sugars present. Using this method with the isolated cellulose enzyme, it will typically be found that 5% cellulosic substrate will remain and at least 90% of the cellulosic substrate will be converted to substantially all glucose.

EXAMPLE 2

I. High Performance Liquid Chromatography Technique

An important tool for the evaluation of cellulolytic activity of the invention and for the characterization of cellulosic substrates, is a high performance liquid chromatography system. Generally, the system applicable here uses a standard arrangement of pumps and eluant containers. The "heart" of the system is the resin column which requires an exhaustive preparation procedure and careful packing.

A cationic exchange resin in its Ca ion form may be utilized for sugar analysis. But, although this provided excellent separations of sugars (cellobiose, glucose, etc.) in pure aqueous solutions, salts and extraneous materials in buffers and culture broth present in the saccharification mixtures caused interference of resolution of some sugars and totally obscured the response of the cello-oligosaccharides of cellulose.

Use of the same resin, but in the H ion form will provide superior results. Instead of water as the eluent, as with the Ca ion form resin, a dilute sulfuric acid (3–5 drops of conc. $H_2SO_4$/liter) is used. The presence of phosphate from the culture medium and buffer, still obscures the resolution of cellobiose. However, by precipitation of the phosphate with cadmium chloride, this interference may be eliminated. The entire complex of salts and other contaminants will elute from the column in the void volume leaving a clear picture of the saccharide components.

Part A

Preparation of Carbohydrate Analysis Column Based upon Ladisch and Tsao, Purdue Univ.

1. Starting material is 50 gm of "Aminex 50W-X4" cationic exchange resin (Purchased in Na ion form from Bio-Rad Laboratories).
2. Wash resin 5 times with specially filtered (Metricel 0.2 micron filter) deionized water. Two liters are used for each wash. (Resin is placed in a 2 L graduated cylinder, mixed and allowed to settle—the wash is removed by aspiration.
3. Suspend the resin in 2 liters of 0.5N HCl (Filtered water and cylinder as above). Allow to settle and aspirate to remove HCl.
4. Repeat step #3 using 1N, 2N, 3N, 4N, 5N and 6N HCl (2 liters of each).
5. Wash with H2O as in step #2 until wash is approximately neutral in pH.
6. Suspend in 2 liters of filtered 0.5% $CaCl_2$ as in step #3, and proceed to 1%, 2%, 3%, 5%, 7% $CaCl_2$.
7. Suspend the resin in 2 L of 10% $CaCl_2$ and heat to 80° C. for 1 hour with stirring (magnetic stirrer). Settle and aspirate.
8. Wash as in step #2, 20–40 times until all "fines" have been removed and wash is clear (A flashlight behind the cylinder is useful). [Settling is for about 6 hours. Towards the end settling in 2–4 hours]
9. Transfer resin to a 125 ml side arm flask, stopper and degas (about 1 hour) under vacuum using or aspirator.
10. Pack (using a packing column) overnight—See Appendix B for packing procedure.

NOTE: If H+ form is desired instead of the Ca ion form, delete steps #5 and #6. Instead heat resin to 80° C. for 1 hour in 6N HCl and then proceed to step #8.

Part B

Packing of the Sugar Column

1. Fill the analytical column (60 cm×6 mm) with eluent (water for Ca ion column or dilute $H_2SO_4$ for H ion column).
2. Attach packing column (60 cm×8 mm) to the top of analytical column.
3. Slurry the resin in as little water as possible and fill packing column with resin using a Pasteur pipette. Tap the column to remove bubbles.
4. Cap the packing column and allow to sit for 30 minutes. Then turn on the thermal controller to heat analytical column to 83° C.
5. Start the eluent flow at 0.1 ml/minute and increase it slowly (say by 0.1 ml increments every 15 minutes) until final flow of 0.7–0.8 ml/minute is reached (back pressure should be about 80–100 PSI). Allow to pack undisturbed overnight at this flow. (Back pressure in morning should be about 100–150 PSI).
6. Reduce flow in increments (always start and stop flow slowly over 15–30 minutes) until stopped.
7. Remove the packing column carefully (analytical column should be full—if not, flush out column and start)
8. Add the top fitting to analytical column, and the guard column and connect to eluent (be sure all air is out of the lines—bubbles should not be permitted in the column)
9. Start flow—increase to 0.5 ml/minute which is the operating flow. Allow column several hours to settle down.
10. Run standards and evaluate "baseline separation" of glucose and cellobiose. (Each at 2 mg/ml: 50 ug sample enters the loop. Sampling holder needs 0.8 ml).

Note 1: It is best to never shut column down completely. At end of day reduce flow to 0.1–0.2 ml/minute and always leave the heater on.

EXAMPLE 3

Pretreatment Of Cellulose

Part A

Cadoxen* Extraction of Cellulose (derived from Methods in Carbohydrate Chemistry Vol. III (H. Wolfson ed) Academic Press)

*Cadoxen is a solution of 30% ethylenediamine/70% $H_2O$ (w/w), to which is added cadmium oxide to saturation.

1. Add 100 ml of Cadoxen reagent to 500 ml flask containing cellulosic substrate (1–5 gm of cellulose)
2. Shake on rotary shaker overnight at ambient temperature (28° used in our tests).
3. Centrifuge at 2000 RPM/10 minutes
4. Decant the Cadoxen solution to 1000 ml flask and fill flask with water. The cellulose will precipitate.
5. Allow the cellulose to settle and wash it until the pH is neutral (centrifugation speeds the process).
6. Add 100 ml fresh Cadoxen solution to the centrifugate (insoluble residue) from step #3 and repeat steps 2–5. (Continue until all cellulose is extracted).
7. Determine cellulose content of final product by the Updegraff method.

Note: The final solution is approximately 5% cadmium. 25% excess CdO is added with constant stirring at room temperature for 30 minutes. Any precipitate is allowed to settle and the Cadoxen solution is decanted. Cadoxen is colorless and odorless (and toxic).

Part B

Preparation of Acid Swollen Cellulose (Walseth)

1. Cool 800 ml of 85% phosphoric acid in an ice bath to 10° C.
2. Add 200 ml of acetone to 100 gm of cellulosic substrate (Whatman CC-41 (alpha-cotton cellulose) is used for the "traditional" Walseth cellulose). Avicel results in a lumpy preparation.
3. Slowly pour the acetone slurry of cellulose into the acid with constant stirring.
4. Stir the mixture constantly for 2 hours in the ice bath.
5. Precipitate the cellulose by adding 1 liter of ice water to above mix.
6. Allow the cellulose to settle and wash it with water and $Na_2CO_3$ and finally just $H_2O$ until the pH is neutral.
7. Determine the cellulose content of crude materials by the Updegraff method, see Table III. (dry weight can be used for pure cellulose e.g. CC-41).

Part C

Delignification and Decrystallization (Holtzapple, Lehigh University)

1. Delignification—ammonia/ethanol (50:50 v/v) at 190° C. for hrs.
2. Swelling—NaOH/ethanol (50:50 v/v) at 160° C. for 30 mins.
−20+40 mesh popular (liquid:wood ratio 10:1).
Ammonia—30% solution (liquid:wood ratio 10:1).
NaOH—30% solution (liquid:wood ratio 10:1).

---

1. Delignification
   0% cellulose loss
   60% hemicellulose loss[1] (WASF)
   70% lignin loss[1] (potassium permanganate oxidation)
2. Swelling
   15% cellulose loss[1]
   65% hemicellulose loss[1] cumulative
   90% lignin loss[1]
3. Swelling
   0.4 g NaOH/g wood      same as above
   delignification        30–40% cellulose loss
   swelling               60–70% hemicellulose loss
                          cumulative loss
                          95% lignin loss
4. Delignified only, Thermomonospora yields 15% hydrolysis (DNS) in 24 hrs
5. Delignified + swollen
   0.2 g NaOH/g wood: 50% hydrolysis in 24 hrs 0.25–0.50 g $H_2O$/g wood 0.4 g NaOH/g wood: 90% hydrolysis in 24 hrs 0.25 g $H_2O$/g wood.
6. Cellulase saccharification at 3% solid and I.U. at = 1.6 gm cellobiose/l enzyme. hr at 55° C. with -glucosidase addition every 2 hrs.

---

[1]TAPPI assays: ile. weak acid susceptible

Example 4

Mutation of M.b.R. Using a Chemical Mutagen

Mutation of *Microbispora bispora* Rutgers P&W using methyl-N'-Nitro-N-Nitrosoguanidine (NTG) may be accomplished in the following manner.

1. Innoculate 50 ml of H/P medium containing 1% cellobiose (no cellulose) with 5 ml of culture: Incubate on shaker at 58° C.
2. Transfer 5 ml to fresh medium after 48 hours. Incubate on shaker at 58° C.
3. After 24 hours add 5 mg NTG to the culture and continue incubation for 30 minutes (N.B. N.T.G. is not sterilized—final conc. = 100 ug/ml).
4. After 30 minutes harvest cells by centrifugation, (2000 rpm/5 minutes).
5. Wash the cells twice with fresh medium.
6. Resuspend in fresh medium and incubate on shaker at 58° C. for 7 hours.
7. Centrifuge at 2000 rpm/5 minutes and discard most of culture broth.
8. Resuspend cells in remaining broth and plate. N.B. N.T.G. is mutagenic and carcinogenic. Exercise extreme caution. Add conc. NaOH to all waste and autoclave to inactivate N.T.G.

What is claimed is:

1. A method for microbial saccharification of a cellulosic substrate which comprises:
   a. inoculating an aqueous nutrient medium with a cellulase-producing microorganism culture selected from the strain *Microbispora bispora* strain Rutgers P&W having accession No. 15568 and mutants thereof which retain cellulolytic activity to produce an inoculated slurry;
   b. fermenting said inoculated slurry at a temperature above about 45° but below about 85° C., at a pH from mildly acidic to mildly basic and for a period of time sufficient to produce a mature culture of microorganisms;
   c. disrupting the cellular membranes of said microorganisms in said mature culture to obtain a saccharification enzyme complex;
   d. combining said saccharification enzyme complex and said cellulosic substrate to form an aqueous mixture; and
   e. maintaining said aqueous mixture at a temperature above about 45° C. but below about 85° C., at a pH from mildly acidic to mildly basic and for a period of time sufficient for hydrolytic conversion of at least some of said cellulosic substrate to glucose.

2. A method according to claim 1 which comprises the additional step of pretreating the cellulosic substrate to enhance subsequent microbial digestion.

3. A method according to claim 2 wherein the pretreatment is acid swelling.

4. A method according to claim 2 wherein the pretreatment is strong acid delignification.

5. A method according to claim 2 wherein the pretreatment is cadoxen extraction.

6. A method according to claim 1 comprising the additional step of filtering the medium to remove undigested cellulosic substrate and a substantial portion of the disrupted microorganism culture to produce an aqueous solution primarily containing glucose.

7. A method according to claim 1 wherein the temperature is from about 45° C. to about 85° C.

8. A method according to claim 1 wherein the pH is from about 5.5 to about 7.5.

9. A method according to claim 1 wherein at least about 80% of the cellulosic substrate is converted to a combination of glucose and cellobiose.

10. A method according to claim 9 wherein at least about 90% of the cellulosic substrate is converted.

11. A method according to claim 10 wherein the mole ratio of glucose to cellobiose produced is at least about 2:1.

12. A method according to claim 11 wherein the ratio is at least 5:1.

13. A method according to claim 12 wherein substantially all of the cellulosic substrate digested has been converted into glucose.

14. A method according to claim 1 wherein the concentration of glucose in the aqueous mixture is at least about 10% after at least about 24 hrs.

15. A method according to claim 14 wherein the concentration of glucose in the aqueous mixture is at least about 16% after at least about 12 hrs.

16. A method according to claim 1 wherein the disrupted microorganism saccharifies a substantial portion of the cellulosic substrate to glucose in the presence of a glucose concentration in the aqueous medium of at least about 10%.

17. A method according to claim 1 wherein the cellulosic substrate is wood pulp, paper pulp, textile pulp, cellulose material, processing waste or municipal refuse.

18. A method for enzymatic saccharification of a cellulosic substrate, which comprises:
 a. combining an aqueous medium of said cellulosic substrate with a cellulase enzyme complex isolated from a cellulase-producing microorganism selected from the strain *Microbispora bispora* Rutgers P&W given accession No. 15568 and mutants thereof which retain cellulolytic activity to produce a hydrolyzing broth; and
 b. maintaining the hydrolyzing broth at a temperature above about 45° C. but below about 85° C., at a pH from mildly acidic to mildly basic and for a period of time sufficient for hydrolytic conversion of at conversion of at least some of said cellulosic substrate to glucose.

19. A method according to claim 18 wherein the enzyme complex is produced by growing the microorganism in a nutrient medium, collecting the secreted components of the complex and after sufficient secreted components have been collected, rupturing the microorganism cells and collecting the cell bound component of the complex.

20. A method according to claim 18 wherein the temperature is from about 45° C. to about 85° C.

21. A method according to claim 18 wherein the pH is from about 5.5 to about 7.5.

22. A method according to claim 18 wherein the concentration of enzyme complex is sufficient to convert at least about 80% of the cellulosic substrate to a combination to glucose and cellobiose.

23. A method according to claim 22 wherein substantially all of the cellulosic substrate hydrolyzed is converted to glucose.

24. A method according to claim 22 wherein the molar ratio of glucose to cellobiose is at least about 2:1.

25. A method according to claim 24 wherein the ratio is at least about 5:1.

26. A method according to claim 18 wherein the enzyme complex saccharifies the cellulosic substrate in the hydrolyzing broth containing at least about 10% glucose.

27. A method according to claim 18 wherein xylonase is isolated along with the cellulase complex and said cellulosic substrate contains xylon.

28. A method for selecting the microoganisms *Microbispora bispora* Rutgers P&W and its mutants which have enhanced cellulolytic activity, from a mixture of thermophilic actinomycetes comprising *Microbispora bispora* Rutgers P&W given accession No. 15568 and mutants thereof which retain cellulolytic activity, which comprises:
 a. inoculating said mixture on a wet cellulosic substrate;
 b. maintaining the inoculated substrate at a temperature of about 45° C. to about 85° C. until spores are produced; and
 c. plating onto a growth-inducing medium containing an ammoniacal source of nitrogen and a cellulosic substrate as the sole source of carbon.

29. A method according to claim 28 which comprises the additional step of transfer of *M. bispora* Rutgers P&W to aqueous liquid culture medium containing K, Mn, Ca, Fe and Na minerals, a phosphate buffer and an ammonium salt.

30. A method according to claim 28 wherein the temperature is about 60° C.

31. A method according to claim 28 wherein the temperature is about 58° C., the time is about 24 hours, and the pH is about 6.5.

32. The microorganisms *Microbispora bispora* Rutgers P&W having accession No. 15568 in a cultured and substantially purified form and mutants thereof which retain cellulolytic activity.

33. The microorganism of claim 32 having spore pairs and being selected by preculturing on a wet legume at a temperature of from about 45° C. to about 85° C.

34. The microorganism according to claim 32 having the ability to grow optimally at about 58° C., having substantial cellulolytic activity which produces primarily glucose, and having substantial resistance to glucose inhibition of its cellulolytic activity.

35. A method for microbial saccharification of a cellulosic substrate which comprises:
 a. inoculating an aqueous nutrient medium with a cellulose-producing microorganism culture selected from the strain *Microbispora bispora* Rutgers P&W having accession No. 15568 and mutants thereof which retain cellulolytic activity to produce an inoculated slurry;
 b. fermenting said inoculated slurry at a temperature of from about 45° C. to about 85° C. and a pH of from about 5.5 to 7.5 to produce a mature culture of microorganisms;
 c. disrupting the cellular membranes of said microorganisms in said mature culture to obtain a saccharification enzyme complex;
 d. combining said saccharification enzyme complex and said cellulosic substrate to form an aqueous mixture; and
 e. maintaining said aqueous mixture at a temperature of from about 45° C. to about 85° C. and a pH of from about 5.5 to 7.5 for about 2 hours to 10 days to convert hydrolytically at least about 90% of said cellulosic substrate to a hydrolysis product comprising substantially all glucose.

36. A method according to claim 35 wherein the cellulosic substrate is pretreated by acid swelling, acid delignification or cadoxen extraction to enhance subsequent microbial digestion.

37. A method according to claim 35 wherein the hydrolysis product is at least about 95% by weight glucose and the glucose concentration in the inoculated slurry is at least about 16% by weight after at least about 12 hours.

38. A method for enzymatic saccharification of a cellulosic substrate, which comprises:
   a. combining an aqueous medium of said cellulosic substrate with a cellulase three-enzyme complex, said complex comprising of endoglucanase, cellobiohydrolase and β-glucosidase, isolated from a cellulase-producing microorganisms selected from the strain *Microbispora bispora* Rutgers P&W having accession No. 15568 and mutants thereof which retain cellulolytic activity to produce a hydrolyzing broth wherein said complex is isolated by a cell free sonicate of said microorganism; and
   b. maintaining the hydrolyzing broth at a temperature of from about 45° C. to about 85° C. and a pH of from about 5.5 to 7.5 for about 2 hours to 10 days to convert at least about 90% of said cellulosic substrate to a hydrolysis product comprising substantially all glucose.

39. A method according to claim 38 wherein the cellulosic substrate is pretreated by acid swelling, acid delignification or cadoxen extraction to enhance subsequent enzymatic hydrolysis.

40. A method according to claim 38 wherein the hydrolysis product is at least about 95% by weight glucose and the glucose concentration in the hydrolyzing broth is at least about 16% by weight after at least about 12 hours.

41. A cellulase three-enzyme complex of endoglucanase, cellobiohydrolase and β-glucosidase, produced by the microorganism *Microbispora bispora* Rutgers P&W having accession No. 15568 and mutants thereof which retain cellulolytic activity, having: a β-glucosidase level of activity of at least about 0.1 unit per ml, as measured by a p-nitrophenyl glucoside substrate assay and as derived from a cell free sonicate produced from a 3 day old cell culture broth; substantial resistance to glucose inhibition of its saccharification activity; a functional temperature range of from about 45° C. to about 85° C.; and a functional pH range of about 5.5 to 7.5.

42. A complex according to claim 41 having a saccharification acitivity in a 10% by weight glucose solution of at least about 65% of its activity in a glucose-free solution.

43. A complex according to claim 41 having a saccharification activity in a 20% by weight glucose solution of at least about 30% to 35% of its activity in a glucose-free solution.

44. A complex according to claim 41 which is isolated from the microorganism *Microbispora bispora* Rutgers P&W or its cellulase-producing mutants.

45. A complex according to claim 41 which is isolated by growing the microorganism in a nutrient medium, collecting the secreted components of the complex, and after sufficient secreted components have been collected, rupturing the microorganism cells and collecting the cell-bound component of the complex.

* * * * *